United States Patent
Ciancia et al.

(10) Patent No.: US 7,932,237 B2
(45) Date of Patent: Apr. 26, 2011

(54) PHARMACEUTICAL COMPOSITIONS FOR USE IN THE TREATMENT OF WOUNDS

(75) Inventors: Marina Ciancia, Buenos Aires (AR); Alberto Cerezo, Buenos Aires (AR); Alberto Luis Moguillansky, Prov. de Buenos Aires (AR)

(73) Assignee: Consejo Nacional De Investigaciones Cientificas Y Technicas (CONICET), Buenos Aires (AR)

( * ) Notice: Subject to any disclaimer, the term of this patent is extended or adjusted under 35 U.S.C. 154(b) by 308 days.

(21) Appl. No.: 12/120,960

(22) Filed: May 15, 2008

(65) Prior Publication Data

US 2009/0286756 A1    Nov. 19, 2009

(51) Int. Cl.
*A01N 43/04* (2006.01)
*A61K 31/715* (2006.01)

(52) U.S. Cl. ............................................. 514/54; 514/25

(58) Field of Classification Search .................. None
See application file for complete search history.

(56) References Cited

OTHER PUBLICATIONS

Kume et al. Agric. Biol. Chem. (1983), vol. 47, pp. 889-890.*
Sen et al. Journal of Biomedical Materials Research (2005), vol. 74A, pp. 187-196.*

* cited by examiner

*Primary Examiner* — Patrick T Lewis
(74) *Attorney, Agent, or Firm* — Young & Thompson

(57) ABSTRACT

A pharmaceutical composition that can be used in the treatment of wounds, comprising at least a sulfated polysaccharide and wherein the polysaccharide/s are in the form of solids as powder, flakes or sheets obtained through a lyophilization process. Particularly, this invention relates to the use of one or more sulfated polysaccharides, as solids in the form of sheets obtained by lyophylization, in the healing of wounds in humans and animals.

10 Claims, 9 Drawing Sheets

Fig. 1A  Most important structures of red alga galactans.
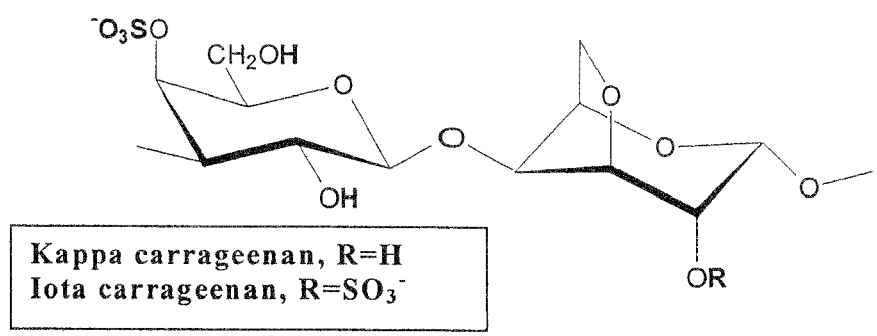
Kappa carrageenan, R=H
Iota carrageenan, R=SO$_3^-$
Fig. 1B
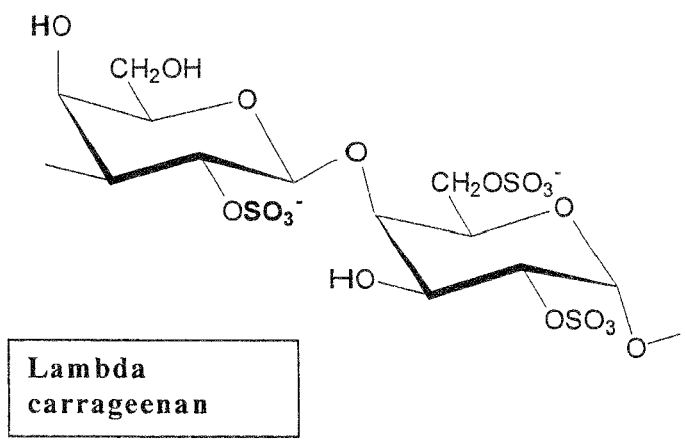
Lambda carrageenan Porphyra Agarosa

PHARMACEUTICAL COMPOSITIONS FOR USE IN THE TREATMENT OF WOUNDS

The present invention relates to a pharmaceutical composition that can be used in the treatment of wounds, that comprises at least one sulfated polysaccharide and wherein the polysaccharide/s are in the form of a solid as powder, flakes or sheets obtained by a lyophylization process. Specifically, the invention relates to the use of one or more sulfated polysaccharides, as a solid in the form of sheets obtained by lyophylization, in the healing of wounds of humans and animals.

BACKGROUND OF THE INVENTION

A) Current Treatments to Stimulate the Granulation Tissue

Different kinds of treatments have been proposed to stimulate the granulation tissue, which is essential to close a wound, as this highly vascularized tissue fills the defects and prepare the surface for epithelization. Among the proposed approaches, we can mention:

a) Treatments to stimulate the granulation tissue: different approaches are being assayed to stimulate the healing processes, being among the most promising ones those using mediators, for example, the recombinant human growth hormone. ("*Effects of recombinant human growth hormone on donor site healing in severely burned children*", Herndon D. N. et al.; 1990; 212: 424-431 and "*Recombinant human growth hormone accelerates wound healing in children with large cutaneous burns*", Gilpin D. A. et al.)

b) Treatments to diminish and module the excessive development of granulation tissue: in the literature it is described the use of topications with 1% silver nitrate. Said compound formulated in the form of a bar is applied in solid state, rubbing the surface of the abundant granulation tissue that hinders the later ephitelization process. In this way, leveling of granulations is sought by the cauterization of the same, thus allowing the advance of the epithelial front ("*Historical review of the use of silver in the treatment of burns*", Klosen H. J. and Burns, March 2000 and "*Reconstructive surgery of the injured nail*", Swanker W. A; The American Journal of Surgery, September 1947).

c) Local use of corticoids: corticoids act as atrophogenic substances, blocking the inflammatory processes involved in the tissue reparation. Therefore, they decrease the presence and advance of "granulations" or angiogenesis. ("*Topical potent corticosteroids for excessive granulation tissue*", Nordir, P. C. et al., Dermatol. Surg. Dec. 24, 1998 (12):1409-10 and "*Topical diflorosone ointment for treatment of recalcitrant, excessive granulation tissue*", Mandrea, E; Dermatol. Surg. Jun. 25, 1999 (6):517)

d) Surgical procedures: they comprise scraping off the hypertrophic granulation tissue by scalpel. Due to the trauma caused by this method, the same must be executed in an operating room under anesthesia. ("*From wound to scar*", Linares, H. A.; Burns, Vol. 22, no 5, pp. 339-352, 1966)

B) Evaluation of the Current Treatments to Stimulate the Granulation Tissue

However, none of the above-mentioned methods is sufficiently efficient. This is due mainly to the following reasons:

a) The silver nitrate produces a chemical destruction of the hypertrophic granulation leaving a contaminated bed, with residues of the product and a secreting trend. In addition, its application frequently is painful and generally must be repeated several times. This compound has no direct action on the vitality of the granulation tissue.

b) Corticoids, due to their atrophogenic action, not only they would tend to diminish the abundance of the tissue under repairing, but also interfere with the process of forming the same, decreasing its vitality and delaying the cellular migration. In the practice, a relative effect is observed with a decrease of the "hypertrophic granules" (insufficient action). In addition, if topication is intense, interference in reparation may be observed.

c) The surgical procedure of scrapping off the granulations using a scalpel, besides being traumatic and troublesome (the patient must be under deep anesthesia or anesthesia) is executed as a previous step to a skin replacement (autograft)

C) Products Proposed to Stimulate the Granulation Tissue. Sulfated Polysaccharides The polysaccharides are polymeric substances formed by units of monosaccharides. There is a great variety of linear or branched polysaccharides, which may be formed by only one type of monosaccharides or different types of monosaccharides. Starch and cellulose are very important members of this kind of compounds. [Aspinall G. O., (1982) "General Introduction" in "The Polysaccharides" (Aspinall G. O., Ed.) Academic Press, Vol I, page 1-17].

Either in the vegetal kingdom, as in the animal kingdom, there exist polysaccharides wherein some hydroxyls are substituted forming sulfate esters. Examples of this kind of polysaccharides are glycosaminoglycans such as heparin, heparan sulfate, etc. which are present in all animal tissues [Fransson L. A., (1988) "Mammalian Polysaccharides" in "The Polysaccharides" (Aspinall G. O., ed.) Academic Press, Vol III, p. 338-406). Also the structure of sulfated polysaccharides has been determined (sulfated L-galactans and L-fucans) in marine invertebrates and, recently, in marine angiosperms [M. S. Pereira, F. R. Melo, and P. A. S. Mourão, "Is there a correlation between structure and anticoagulant action of sulfated galactans and sulfated fucans", Glycobiology, 12, 573-580 (2002); R. S. Aquino, A. M. Landeira-Fernandez, A. P. Valente, L. R. Andrade, and P. A. S. Mourao, "Occurrence of sulfated galactans in marine angiosperms: evolutionary implications", Glycobiology, 15, 11-20 (2005)].

In the algae, they are the principal constituents of the intercellular matrix and the cellular wall, and in some cases, such as in red algae, they represent more than 50% dry weight of the alga. [Painter T. J., (1988) "Algal polysaccharides" in "The Polysaccharides" (Aspinall G. O., ed.) Academic Press, Vol II, page 196-27].

It has been demonstrated that these polysaccharides have a great variety of biological properties, such as antiviral, antitumor, antioxidant, anticoagulant, antithrombotic activities, etc. [Damonte E. B., Matulewicz, Cerezo A. S., (2004) "Sulfated seaweed polysaccharides as antiviral Agents", Current Medicinal Chemistry, 11, 2399-2419]. [Alban S., (1997) "Carbohydrates with anticoagulant and antithrombotic properties" in "Carbohydrates in Drug Design" (Witczak Z. J. and Nieforth K. A., eds.) Marcel Dekker, Inc. page 209-277] [Witvrouw M., Pannecouque C., De Clercq E., (1997) "Polysulfates: Chemistry and Potential as Antiviral Drugs" in "Carbohydrates in Drug Design"; I. M. Yermak and Y. S. Khotimchenko, in Recent Advances in Marine Biotechnology, Vol. 9 Biomaterials and Bioprocessing, ed. M. Fingerman and R. Nagabhushanam Science Publishers Inc. 2003, Enfield (N.H.) USA, "Chemical Properties, Biological activities and applications of carrageenans from red algae", p. 207-255]

However, not all of these compounds show the same degree of activity and their behavior is related to the position and degree of sulfatation. In addition, it has been demonstrated that artificially sulfated polysaccharides and even sulfated synthetic polymers show, in some cases, similar activities. [Damonte E. B., Matulewicz, Cerezo A. S., (2004) "Sulfated seaweed polysaccharides as antiviral Agents", Current Medicinal Chemistry, 11, 2399-2419] [Alban S., (1997) "Carbohydrates with anticoagulant and antithrombotic properties" in "Carbohydrates in Drug Design" (Witczak Z. J. and Nieforth K. A., eds.) Marcel Dekker, Inc. page 209-277.] [Witvrouw M., Pannecouque C., De Clercq E., (1997) "Polysulfates: Chemistry and Potential as Antiviral Drugs" in "Carbohydrates in Drug Design"; I. M.].

The sulfated galactans comprise the cellular matrix of most of the red algae. They are linear polysaccharides formed by alternating units of β-D-galactopyranose bound by position 3 and α-(3,6-anhidro)galactopyranose bound by position 4. Polysaccharides wherein units α are in configuration D are known as carrageenans, while when this unit is in configuration L, they are aragans, being agarose the most known member of this family of polysaccharides, that is not sulfated. The agarans and carrageenans are sets of different polysaccharides having similar hydrocarbon skeletons and different type and position of substitution, which results in important variations in their physical properties and biological activity. Thus, carrageenans are classified in different families according to the function of the sulfatation position in the β-galactose unit. Carrageenans of the kappa family are those wherein this unit is sulfated in C-4, kappa and iota carrageenans belong to this family. Moreover, lambda carrageenans are characterized by the sulfatation in C-2 of the unit β, being the most important member of this family the lambda carrageenan (FIG. 1). Besides the sulfatation position, the kappa carrageenan has only one sulfate group by repetitive disaccharide unit, the iota two and the lambda, three. Kappa and iota repeating disaccharide units may coexist in the same carrageenan, which is indicated as a kappa/iota hybrid. [C. A. Stortz and A. S. Cerezo, "Novel findings in carrageenans, agaroids and "hybrid" red seaweed galactans", Current Topics in Phytochemistry, 4, 121-134 (2000)].

BRIEF SUMMARY OF THE INVENTION

The present invention relates to a pharmaceutical composition that can be used in the treatment of wounds, comprising at least one sulfated polysaccharide and wherein the polysaccharide/s is/are as solids in the form of powder, flakes or sheets. Specifically, the invention relates to the use of sulfated polysaccharides, as solids in the form of lyophilized, dehydrated and sterilized sheets, over traumatic cutaneous wounds, such as, for example, intermediate and deep burns, and over non-traumatic wounds, such as venous ulcers.

BRIEF DESCRIPTION OF THE DRAWINGS

The present invention will be described in connection with the attached drawings, in which:

FIGS. 1A-1D illustrate the most important structures of red alga galactans;

DETAILED DESCRIPTION OF THE INVENTION

Figure 1C:
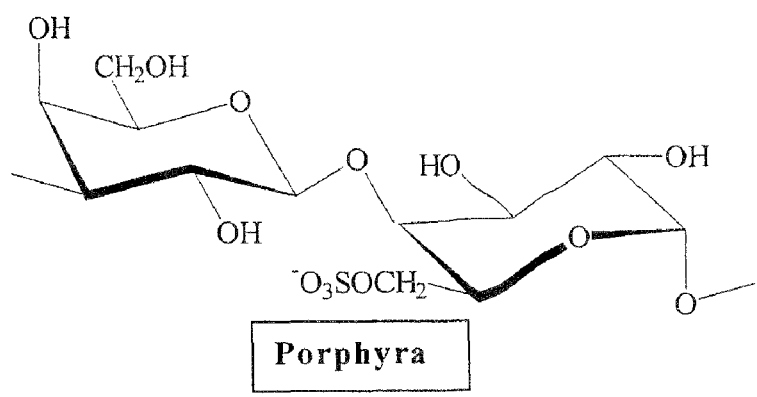
Figure 1D:
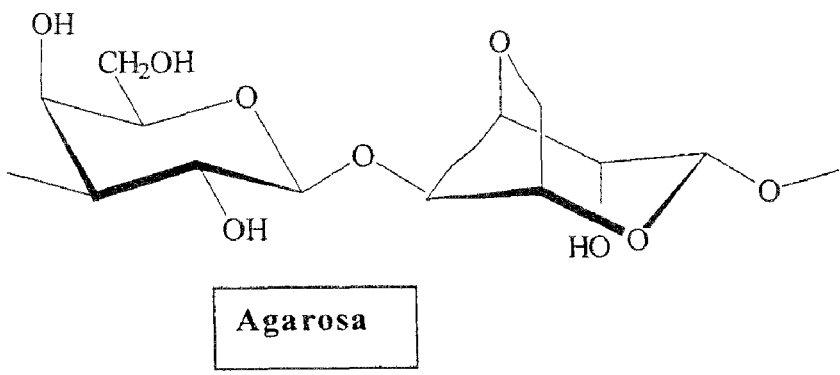

In a particular embodiment of the invention, from the group of sulfated polysaccharides, preferred members are kappa or iota carrageenans or hybrids thereof and lambda carrageenans obtained from red algae of the species *Iridaea, Gigartina, Eucheuma* and *Kappaphyccus*.

Closing of wounds occurs when, among other multiple and complex biological processes, the granulation tissue advances over the bed of wounds, as a protagonist of the intermediate step of healing. The granulation tissue is a highly cellular, vascular and functional structure primarily devoted to clean the damaged area, fills the existing tissue defect and supports the development of new and active tissue of the mesenchyme. However, the bed of a wound may show different aspects that reveal the status and the course of action of this tissue and scarring development. In relation with the granulation tissue, an anatomoclinic distinction between at least two forms of presentation of the bed under repairing has to be made:

1) A wound with a flat, pale and low vital bed, that tends to delay appearance of the suitable granulation tissue to start the process of repairing by production of the extracellular matrix; such as, for example: the bed of a deep intermediate burn (classification from the American Burn Association) (or type AB according to the classification of Benaim); or torpid scar beds as in venous ulcers and similar.

2) A wound with hypertrophic granulation tissue (uncontrolled growth). The excess of granulation tissue (hypertrophic granulation) prevents the potential epithelization action (progression of epithelial cells from anexial reservoirs and/or the cutaneous edges of a wound) spreads covering a bleeding bed with epithelial cells devoted to close the wound.

The inventors of the present invention have found that the above-mentioned cases can be successfully treated applying the composition of the invention.

The present invention relates to a pharmaceutical composition that can be used in the treatment of wounds, comprising at least a sulfated polysaccharide and wherein the polysaccharide/s is/are in a solid form as powder, flakes or sheets obtained by a lyophylization, dehydration and sterilization process. Particularly, the invention relates to the use of solid sulfated polysaccharides, such as sheets obtained by lyophylization, dehydration and sterilization, over traumatic cutaneous wounds, such as for example intermediate and deep burns, and non-traumatic wounds, for example venous ulcers.

In a particular embodiment of the invention, from the group of saturated polysaccharides, kappa or iota carrageenans or hybrids thereof are preferred, as well as the lambda carrageenans obtained by extraction with water at ambient temperature or heat and removing the products of low molecular weight, of red algae of the species *Irideae, Gigartina, Eucheuma* and *Kappaphyccus*.

Carrageenans are compounds that are industrially extracted with alkaline aqueous solutions of different species of red algae (rodoficeae) usually pretreated also with alkali, and used in different industries such as the food and cosmetic industries, etc. as thickening and/or gelling agents. Carrageenans obtained under these conditions require heating to dissolve in water, but when cooled form gels, which rheological parameters depend on the concentration of polymer and number of potassium, ammonium or calcium ions contained by the hydrocolloid.

Thus, a wound with a flat, pale and low vital bed, that tends to delay appearance of the suitable granulation tissue to start the process of repairing by production of the extracellular matrix, could be treated with the composition of the invention, by applying locally sheets of lyophilized, dehydrated and sterilized carrageenans over the devitalized bed of the wounds by the scrapping procedure.

Moreover, a wound with hypertrophic granulation tissue, could be treated with the composition of the invention, by applying topically the same preparations over the hypertrophic granulation tissue, allowing in this way to control its volume and harmonize development of the same.

Both application procedures are to increment vitality and control the development of the repairing tissue producing in a lesser time the extracellular matrix and closing of the wound. The contact of carrageenans, prepared as previously described, with the surface to treat produces a sensible adherence to the same, and so the scrapping off procedure must be executed firmly, obtaining a bleeding of the bed partially due to the traumatic action over the cellular coating of granulation tissue on which the carrageenan preparation has "adhered", and partially to an anticoagulant property of the carrageenan. The beneficial effects would be the result of the contact of blood with all the surface of the wound, transporting growth and stimulating factors; as well as of an own and direct action of the carrageenan preparation, as the simple scrapping mechanism does not attain the effects herein obtained.

This form of use usually is complemented with a later application of said preparation in the form or sheets, that are left as a biological dressing over the treated surfaces between 24 to 72 hours, and as a complement of the previous treatment. In this way, it is possible to reduce progressively the abundance of an exceeded granulation tissue, allowing the advance of the epithelium from the extensions and the edges of the wound treated to complete healing.

EXAMPLE

The carrageenan samples used in the first case correspond to a kappa/iota hybrid carrageenan extracted from cystocarpic specimens of the red alga *Gigartina skottsbergii*, collected in Bahía Camarones, Chubut (Argentina).

The agarose, which is a neutral polysaccharide, without sulfate groups, but with a chain similar to the carrageenans (the unit of α-galactose is in L configuration instead of D) showed no activity and the results with sodium alginate were not conclusive. Notwithstanding the latter polysaccharide is acid, it does not have sulfate groups and its acidity is due to the presence of the carboxyl groups of the uronic acids forming the same.

Figure 2A:
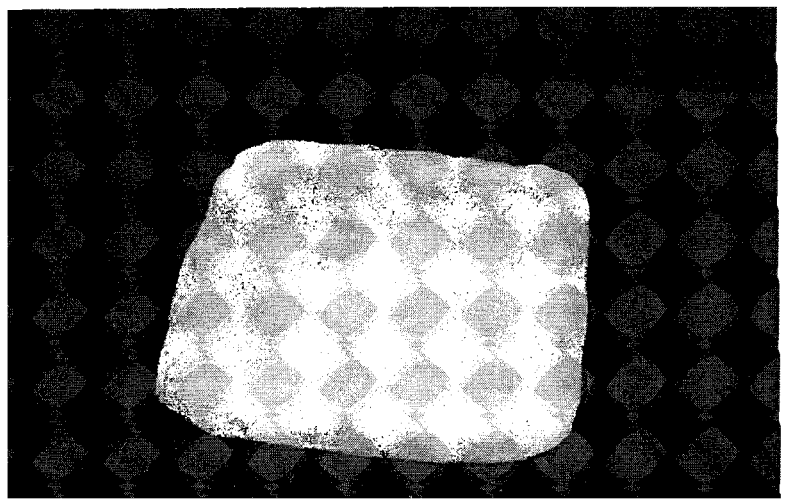
FIGS. 2A-2C illustrate Lyophilized carrageenans prepared according to the described procedure.
Figure 2B:
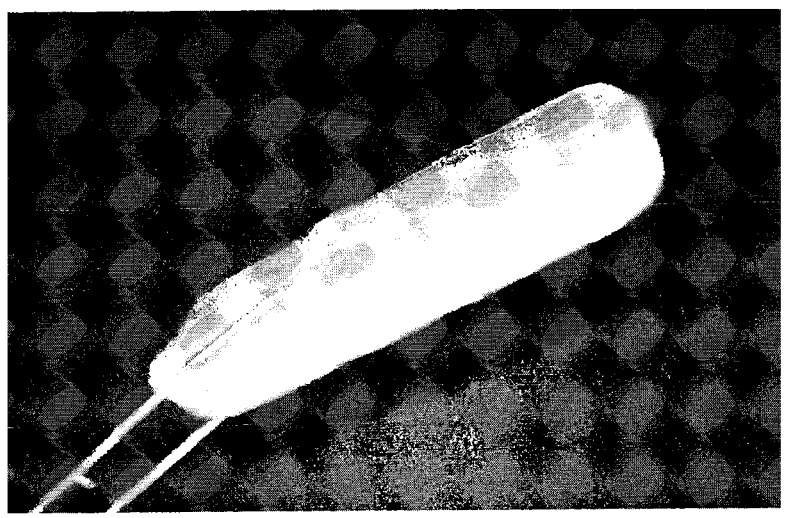
Figure 2C:
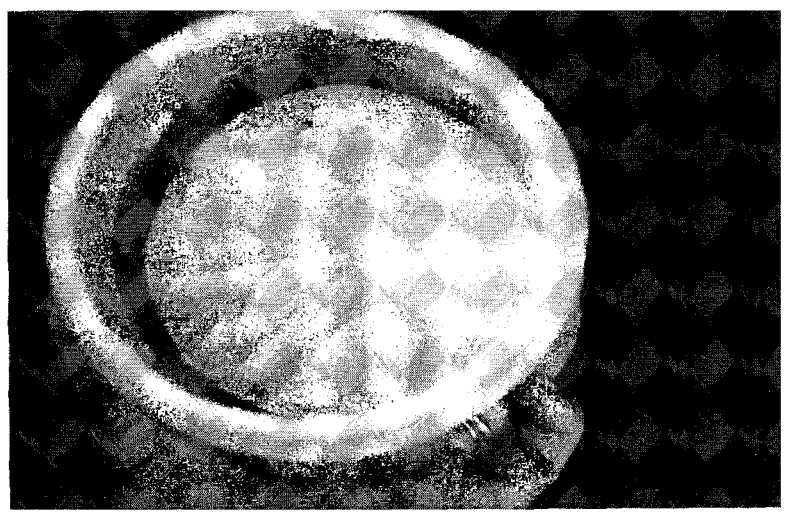
Figure 3:
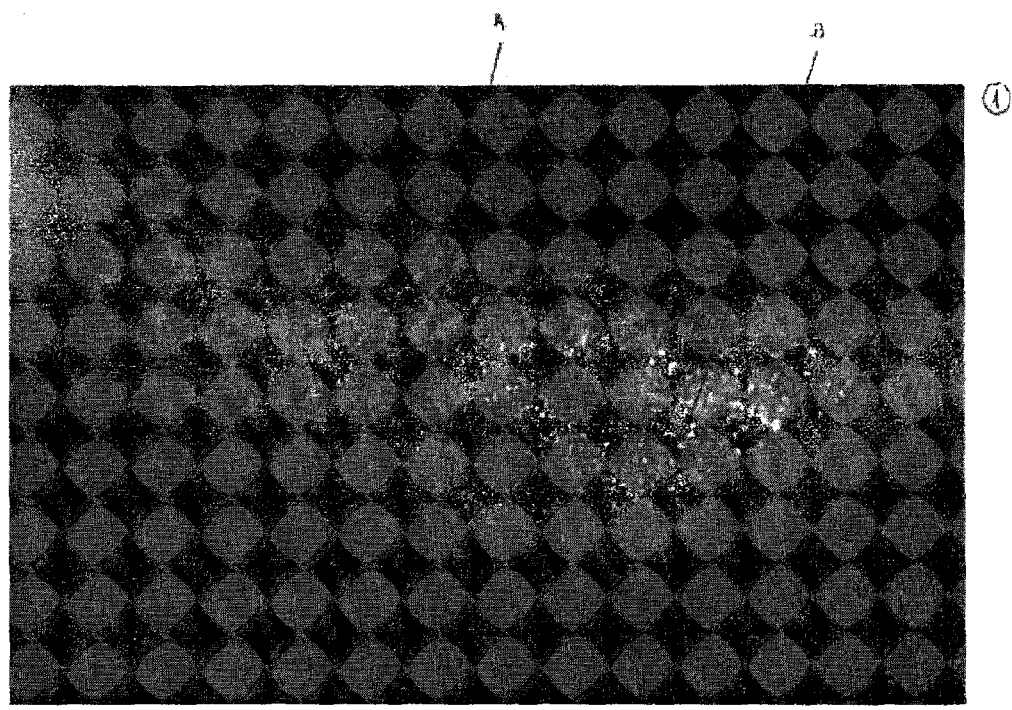
FIGS. 3-12 are photographic images of right lower third of an arm, elbow and upper third of a forearm, of a patient illustrating treatment of a wound over time.
Figure 4:
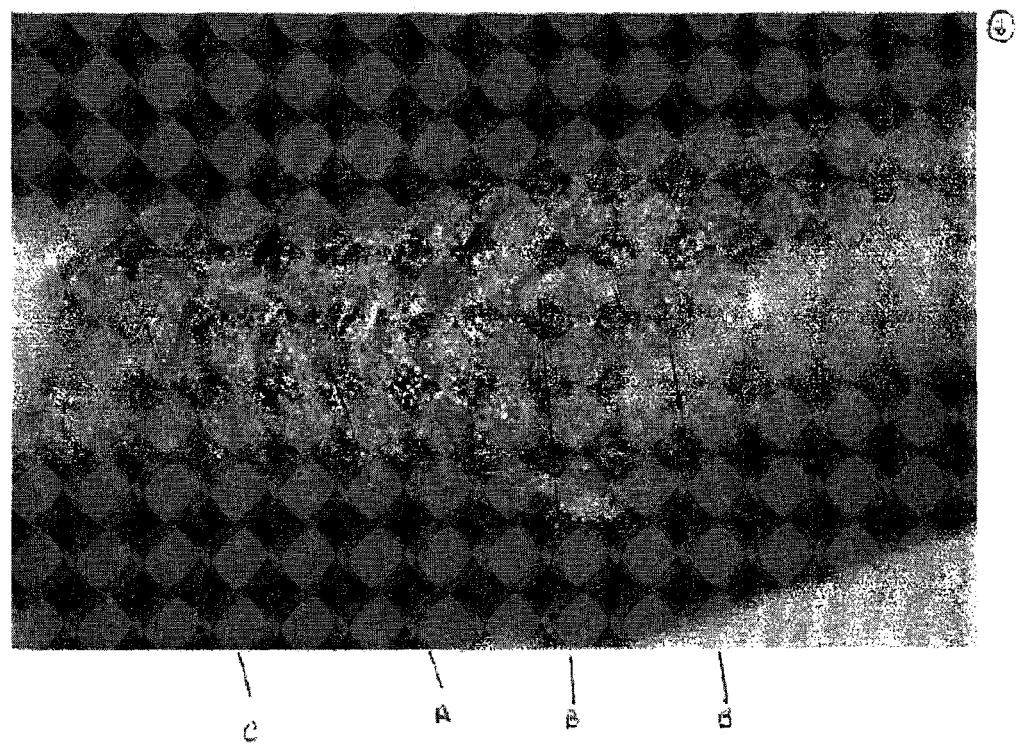
Figure 5:
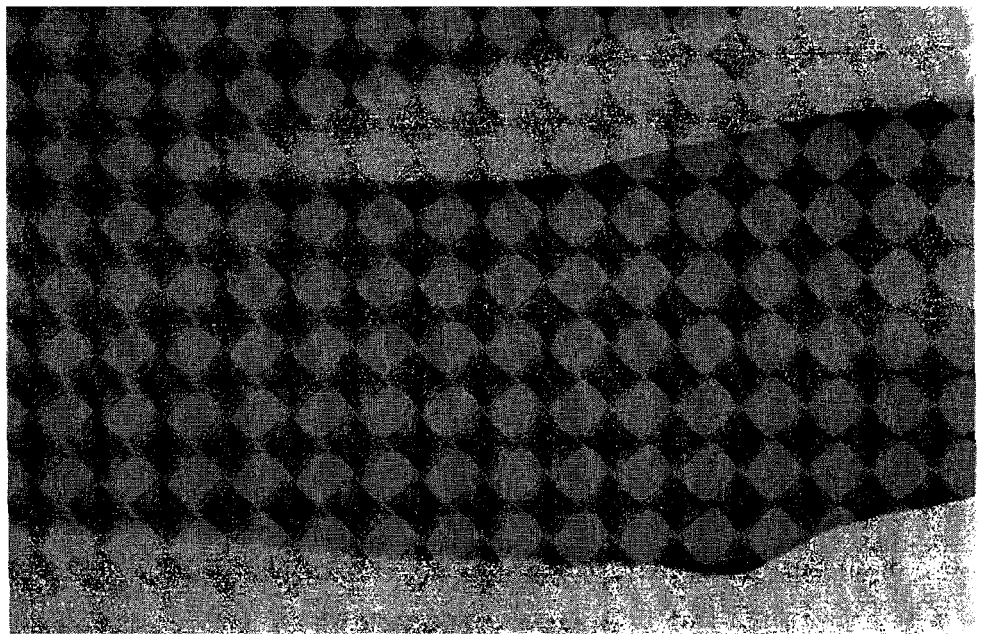
Figure 6:
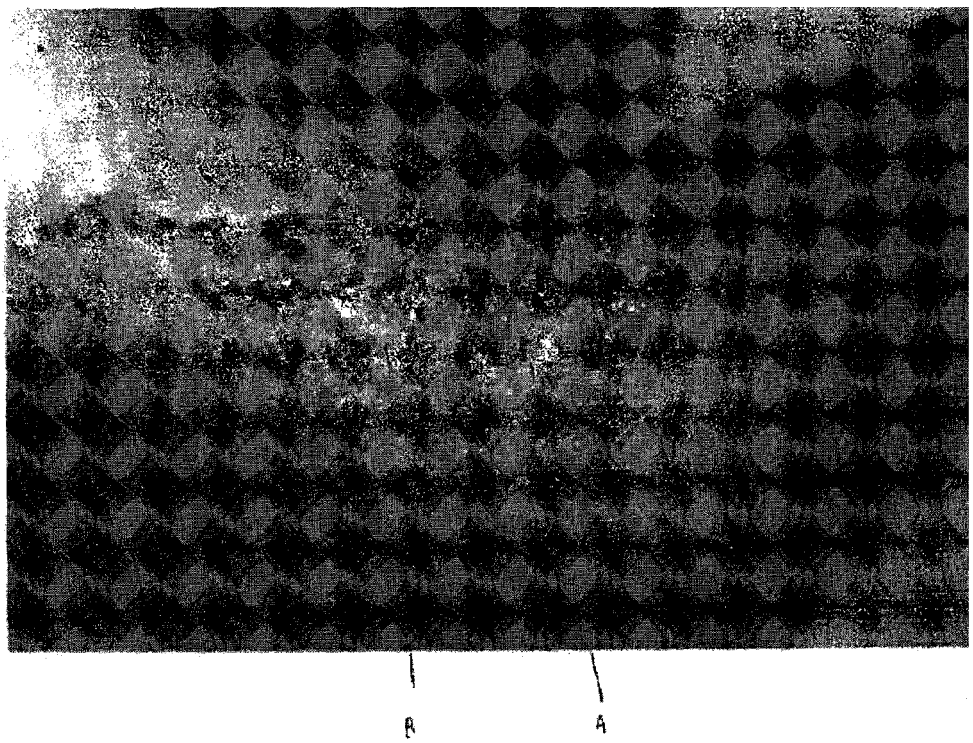
Figure 7:
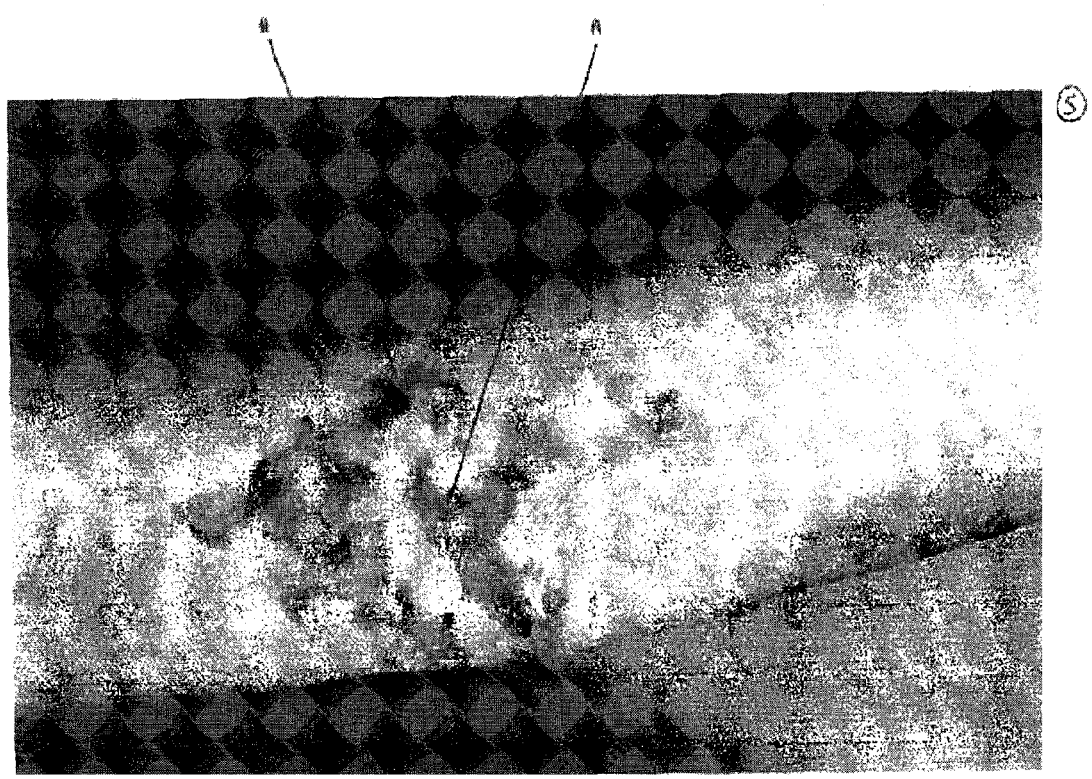
Figure 8:
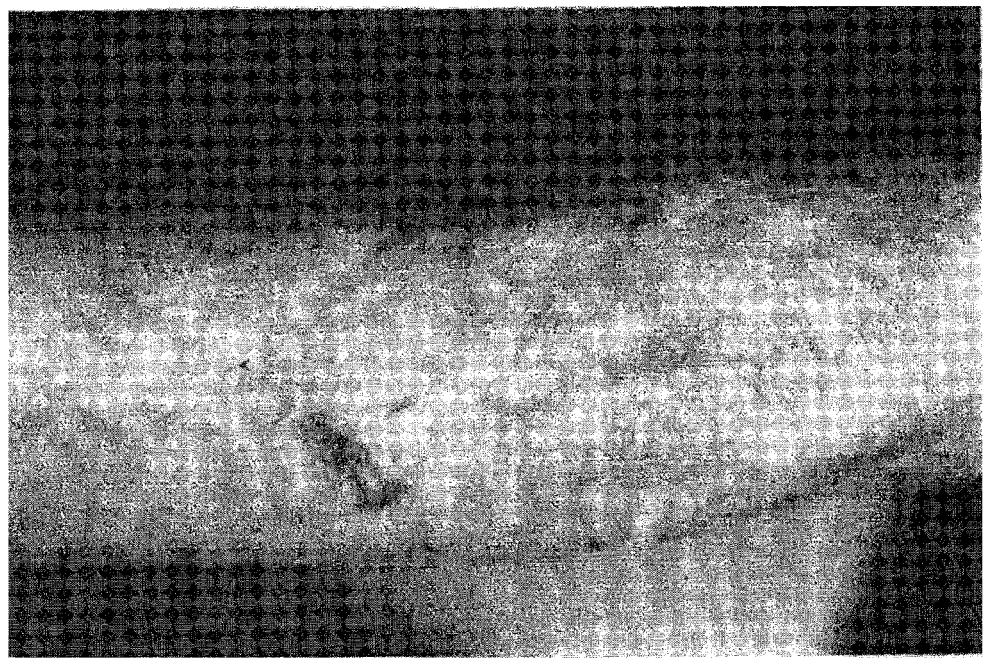
Figure 9:
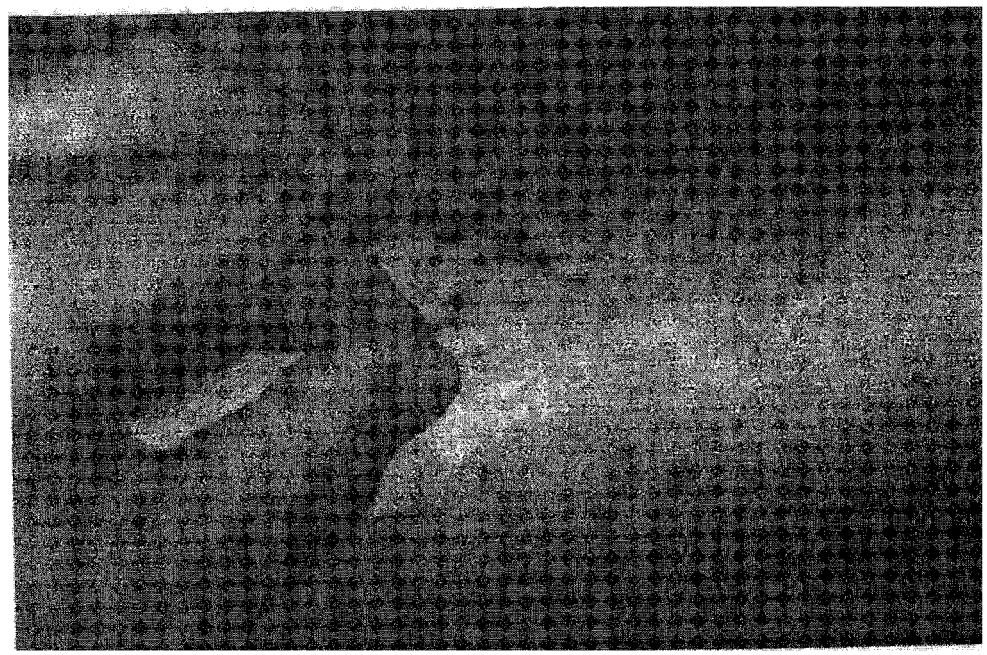
Figure 10:
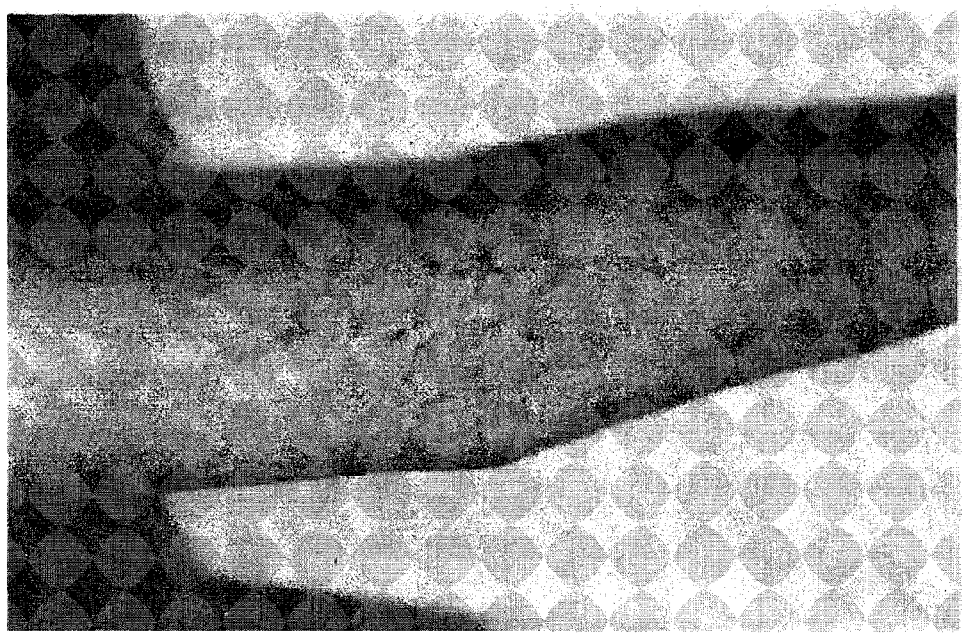
Figure 11:
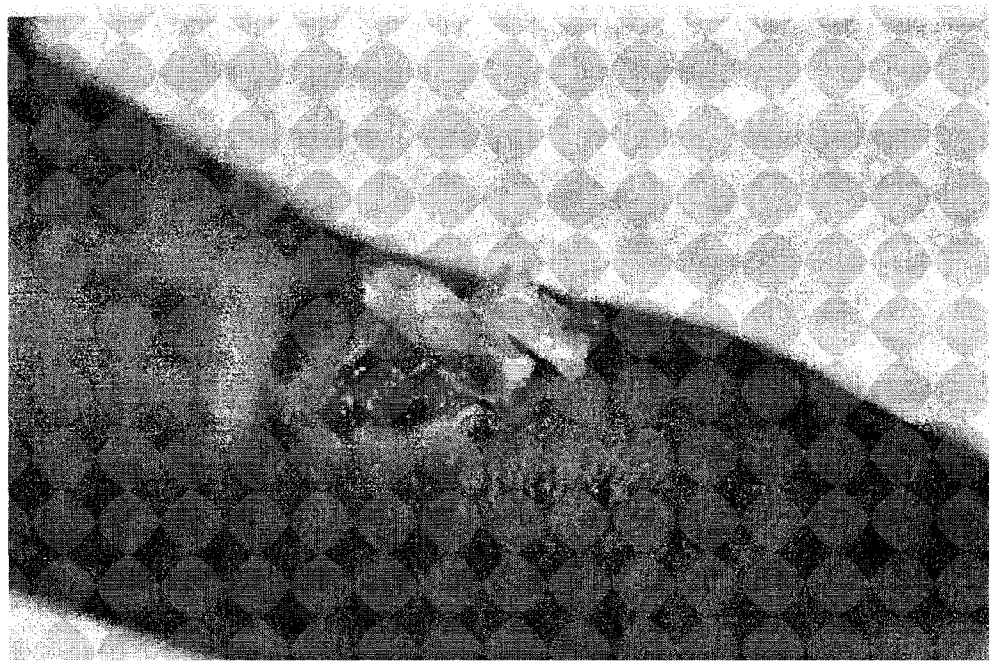
Figure 12:
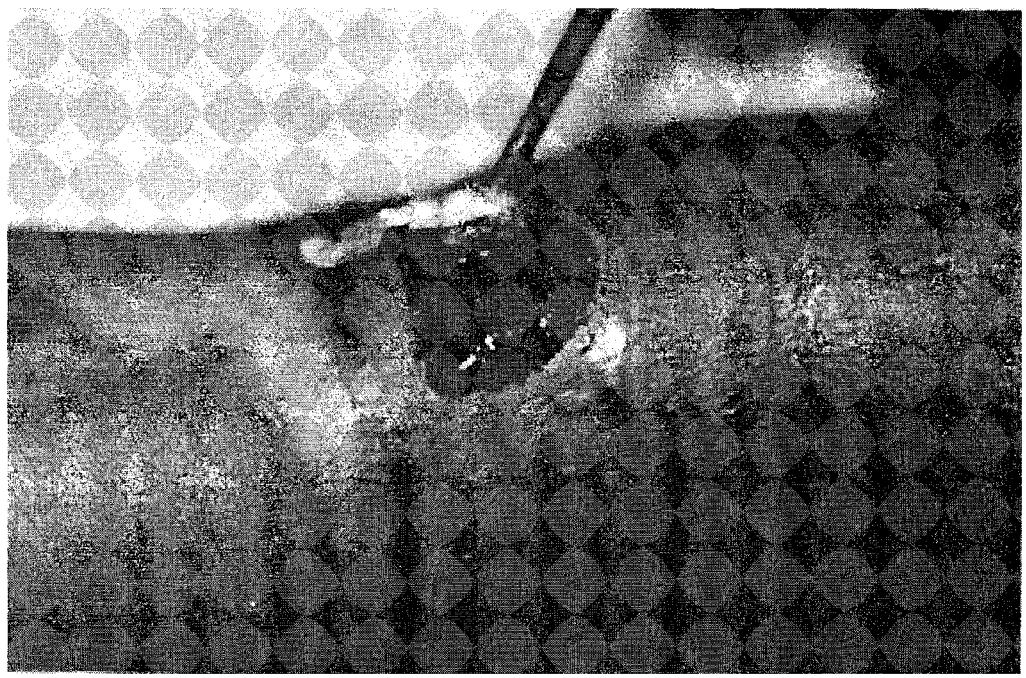

1) Procedure to prepare sheets of lyophilized, dehydrated and sterilized carrageenans from cystocarpic specimens of red alga *Gigartina skottsbergii*:

The dry alga was grinded using a Wiley mill (20-mesh screen). Thereafter, the grinded alga (50 g) was suspended in water (2.5 l) and extracted under mechanical stirring at ambient temperature during 16 hours. The mixture was centrifuged at 8000 rpm at a temperature of 10° C. and the supernatant was concentrated to half of its volume removing the products of low molecular weight by dialysis (MWCO 12-14000). The solution was lyophilized in plastic trays of suitable dimensions and forms, obtaining a spongy product of high contact surface, of about 1-2 cm of height and a surface of 10×10 cm, which was later dehydrated and sterilized, and fractioned as needed (FIG. 2).

It is very important that the solution to lyophilize has such a volume and concentration that the final lyophilized, dehydrated and sterilized product has the largest contact surface and the adequate consistency so as to be applied to the wound, that is scrapped off as previously described, and then the product is left, as a biological dressing, on the wound during 72 hours without disintegrating.

2) Treatment of wounds using carrageenans

Devitalized or hyper granulating beds (photograph number 1: image of right lower third of an arm, elbow and upper third of a forearm, of a patient of 50 years old burnt with hot water 16 days ago, resulting in a lesion equivalent to 2% of the body surface, type deep intermediate and deep according to the classification of the American Burn Association [or AB and B according to the classification of Benaim]. At ["A"] rests of B or deep scar with devitalized and necrobiotic tissue are observed, and at "B" incipient pale and hypertrophic granulation tissue).

Application of carrageenans in powder, flake or sheet forms (photograph number 9 shows the use of pieces of carrageenans over the burn of another patient), by scrapping (photograph number 10 with the same patient showing the surface already stimulated and bleeding resulting from the above described use).

Stimulation and control of granulation tissue development (photograph number 2 of the patient initially selected at day 7 and after receiving two applications of carrageenans. It is observed in ["A"] a complete change in the evolution of a bed that in spite of showing more reduced rests of B scars, it is controlled by the development of a suitable granulation tissue allowing the advance of marginal ["C"] and eccentric ["B"] epithelization from the annexial epithelial rests).

Improvement of beds with the appearance of convergent epithelial islands, resulting from stimulating the epithelial reservoir of non-destroyed extensions (photograph number 3 18 days after the start of the treatment with an epithelized surface of about 80%). Carrageenans were applied between 48 and 72 hours.

Gradual epithelial healing with advance of convergent and divergent epithelium (photograph number 4 with 90% of the surface epithelized; though persistent rests of deep beds or B in late spontaneous removal stage ["A"] are still observed). Twenty-two days of progress. Photograph number 5 shows the same tendency, days after (["A"] shows small rests of scar that have not been self-removed yet).

Complete closing of the wound with reduction of healing times (photograph number 6), after almost one month of treatment.

Reduction of effects (photograph number 7 shows a post-healing skin having a good consistency and flexibility).

Optimization of esthetic and functional healing results (photograph number 8 taken two months after the start of treatment).

CONCLUSIONS

The conclusions obtained from this example can be extended to other sulfated polysaccharides, as many of them have similar biological activities. Said biological activities are attributed to the presence of sulfate groups, though they many express to a greater or lesser extent depending on: a) the degree of sulfatation, b) the position of sulfatation, c) the linear or branched structure of the compound, d) the molecular weight.

Therefore, it is considered that every sulfated polysaccharide that may be obtained under the above-described conditions could be used in the claimed pharmaceutical composition to promote healing of wounds by the disclosed procedure. The above considerations can be extended to other sulfated polymers that meet the indicated conditions, even though they are not polysaccharides.

What is claimed is:

1. A pharmaceutical composition that can be used in the treatment of wounds, comprising a sulfated polysaccharide, wherein the sulfated polysaccharide is in the form of solids as flakes or sheets obtained by lyophilizing, dehydrating and sterilizing a solution of the sulfated polysaccharide.

2. A pharmaceutical composition that can be used in the treatment of wounds, according to claim 1, wherein the sulfated polysaccharide is in the form of sheets.

3. A pharmaceutical composition that can be used in the treatment of wounds, according to claim 1, wherein the sulfated polysaccharide is selected from kappa, iota, kappa/iota or lambda carrageenans.

4. A pharmaceutical composition that can be used in the treatment of wounds, according to claim 1, comprising a mixture of sulfated polysaccharides.

5. A pharmaceutical composition that can be used in the treatment of wounds, according to claim 1, wherein the sulfated polysaccharide is a carrageenan.

6. A wound dressing, comprising a solid form of a sulfated polysaccharide.

7. The wound dressing according to claim 6, wherein the sulfated polysaccharide is a carrageenan.

8. The wound dressing according to claim 6, wherein the sulfated polysaccharide is selected from the group consisting of kappa, iota, kappa/iota and lambda carrageenans.

9. The wound dressing according to claim 6, wherein the sulfated polysaccharide is obtained by lyophilizing, dehydrating and sterilizing a solution of the sulfated polysaccharide.

10. The wound dressing according to claim 6, wherein the solid form of sulfated polysaccharide is a sheet.

* * * * *